United States Patent
Simmons

(10) Patent No.: US 11,800,941 B2
(45) Date of Patent: Oct. 31, 2023

(54) COOLING AND WARMING COVER EMBEDDED WITH TUBING FILLED WITH LIQUID

(71) Applicant: Brenda Simmons, Carmel by the Sea, CA (US)

(72) Inventor: Brenda Simmons, Carmel by the Sea, CA (US)

( * ) Notice: Subject to any disclaimer, the term of this patent is extended or adjusted under 35 U.S.C. 154(b) by 623 days.

(21) Appl. No.: 16/744,173

(22) Filed: Jan. 15, 2020

(65) Prior Publication Data

US 2021/0212480 A1    Jul. 15, 2021

Related U.S. Application Data

(60) Provisional application No. 62/792,871, filed on Jan. 15, 2019.

(51) Int. Cl.
*A47G 9/02* (2006.01)
*A42B 3/28* (2006.01)

(52) U.S. Cl.
CPC ............ *A47G 9/0215* (2013.01); *A42B 3/285* (2013.01); *A42B 3/286* (2013.01)

(58) Field of Classification Search
CPC ...... A47G 9/0215; A42B 3/285; A42B 3/286; A41D 13/005; A41D 13/0051; A41D 13/0053
See application file for complete search history.

(56) References Cited

U.S. PATENT DOCUMENTS

| | | | | |
|---|---|---|---|---|
| 3,211,216 A | * | 10/1965 | Coleman, Jr. | A41D 13/005 165/46 |
| 3,425,486 A | * | 2/1969 | Burton | B64D 10/00 165/DIG. 46 |
| 4,662,433 A | * | 5/1987 | Cahn | A47C 21/044 607/104 |
| 4,691,762 A | * | 9/1987 | Elkins | A41D 13/0053 607/108 |
| 5,291,750 A | * | 3/1994 | Parrish | A41D 13/005 62/480 |
| 5,320,164 A | * | 6/1994 | Szczesuil | A41D 13/005 165/46 |
| 5,658,325 A | * | 8/1997 | Augustine | A47G 9/0215 607/104 |
| 5,989,285 A | * | 11/1999 | DeVilbiss | A61F 7/0097 607/104 |
| 6,105,382 A | * | 8/2000 | Reason | A41D 13/005 165/46 |
| 6,109,338 A | * | 8/2000 | Butzer | A41D 13/005 607/104 |

(Continued)

FOREIGN PATENT DOCUMENTS

| | | | | |
|---|---|---|---|---|
| GB | 2274239 A | * | 7/1994 | ........... A41D 13/005 |
| WO | WO-2013076628 A1 | * | 5/2013 | ........... A47C 21/048 |
| WO | WO-2018075579 A1 | * | 4/2018 | ............... A61F 7/00 |

*Primary Examiner* — Alissa L Hoey

(57) ABSTRACT

A cover for human and domestic mammals, which provides cooling and warming to a wearer utilizing tubing attached to the cover and filled with liquid. The liquid is distributed throughout the tubing by a pump and the temperature of the liquid is controlled by a thermostat. The cover and pump are portable wherein the pump is housed in a carrying bag. The pump is interchangeable with additional covers for heating and cooling as desired.

1 Claim, 1 Drawing Sheet

(56) References Cited

U.S. PATENT DOCUMENTS

| | | | | |
|---|---|---|---|---|
| 6,565,699 B1* | 5/2003 | Szczesuil | B29C 66/1122 | 156/290 |
| 6,942,015 B1* | 9/2005 | Jenkins | A42B 3/285 | 2/458 |
| 6,957,697 B2* | 10/2005 | Chambers | F28F 21/00 | 165/46 |
| 7,089,995 B2* | 8/2006 | Koscheyev | A61F 7/02 | 607/104 |
| 7,681,249 B2* | 3/2010 | Oliver | B64D 10/00 | 2/102 |
| 7,765,616 B2* | 8/2010 | Gammons | A41D 13/005 | 2/115 |
| 7,823,625 B2* | 11/2010 | Gammons | F16L 37/0841 | 165/46 |
| 8,397,517 B2* | 3/2013 | Monk | A41D 13/005 | 62/3.5 |
| 9,072,577 B1* | 7/2015 | Ferko, III | A61F 7/00 | |
| 10,477,978 B1* | 11/2019 | Youngblood | A47C 21/04 | |
| 10,721,977 B2* | 7/2020 | Gueritee | H05B 1/0272 | |
| 10,980,292 B2* | 4/2021 | Fan | A61F 7/02 | |
| 11,047,626 B2* | 6/2021 | Saavedra | F24T 10/10 | |
| 11,247,115 B2* | 2/2022 | Blecher | A42B 3/225 | |
| 11,297,693 B2* | 4/2022 | Zhang | A41D 13/0053 | |
| 11,330,852 B2* | 5/2022 | Luo | F24F 5/001 | |
| 11,633,053 B2* | 4/2023 | Youngblood | A61B 5/0024 | 62/3.5 |
| 2002/0153126 A1* | 10/2002 | Clemente | F25B 27/00 | 607/104 |
| 2006/0107679 A1* | 5/2006 | Pohr | F24F 5/0017 | 62/424 |
| 2008/0040839 A1* | 2/2008 | Gordon | A41D 13/0053 | 607/108 |
| 2010/0084125 A1* | 4/2010 | Goldstein | F17C 11/00 | 62/3.5 |
| 2010/0107657 A1* | 5/2010 | Vistakula | A41D 13/0056 | 62/3.5 |
| 2010/0223943 A1* | 9/2010 | Loukaides | A41D 13/0053 | 62/259.3 |
| 2010/0281883 A1* | 11/2010 | Romano | A41D 13/005 | 62/3.5 |
| 2011/0277485 A1* | 11/2011 | Yang | F28F 1/22 | 62/3.2 |
| 2012/0036623 A1* | 2/2012 | Minogue | A41D 31/102 | 2/463 |
| 2012/0227432 A1* | 9/2012 | Creech | A41D 13/0053 | 62/259.3 |
| 2013/0019611 A1* | 1/2013 | Sims | A41D 13/005 | 165/41 |
| 2014/0201891 A1* | 7/2014 | Turner | A41D 13/015 | 2/455 |
| 2014/0222121 A1* | 8/2014 | Spence | A61F 7/02 | 607/104 |
| 2015/0075185 A1* | 3/2015 | Sims | F25B 21/04 | 62/3.5 |
| 2015/0237927 A1* | 8/2015 | Nelson | A41D 13/005 | 5/413 R |
| 2015/0320588 A1* | 11/2015 | Connor | A61F 7/0085 | 607/104 |
| 2016/0029808 A1* | 2/2016 | Youngblood | F25D 29/00 | 62/3.2 |
| 2016/0206018 A1* | 7/2016 | Barbret | A41D 13/0053 | |
| 2017/0105870 A1* | 4/2017 | Yazdani | A43B 3/36 | |
| 2018/0014585 A1* | 1/2018 | Polonio | A41D 27/00 | |
| 2019/0104774 A1* | 4/2019 | Paiva | A61F 7/02 | |
| 2019/0137160 A1* | 5/2019 | Larsen | F25D 3/08 | |
| 2019/0374377 A1* | 12/2019 | Mcgregor | A61F 7/0097 | |
| 2020/0329788 A1* | 10/2020 | Su | A41D 13/0053 | |
| 2021/0037900 A1* | 2/2021 | Itao | A61F 7/007 | |
| 2021/0127762 A1* | 5/2021 | Mach | A41D 13/0053 | |
| 2021/0352974 A1* | 11/2021 | Kirchmeier | A41D 13/005 | |
| 2023/0051351 A1* | 2/2023 | Pare | A45F 3/04 | |

\* cited by examiner

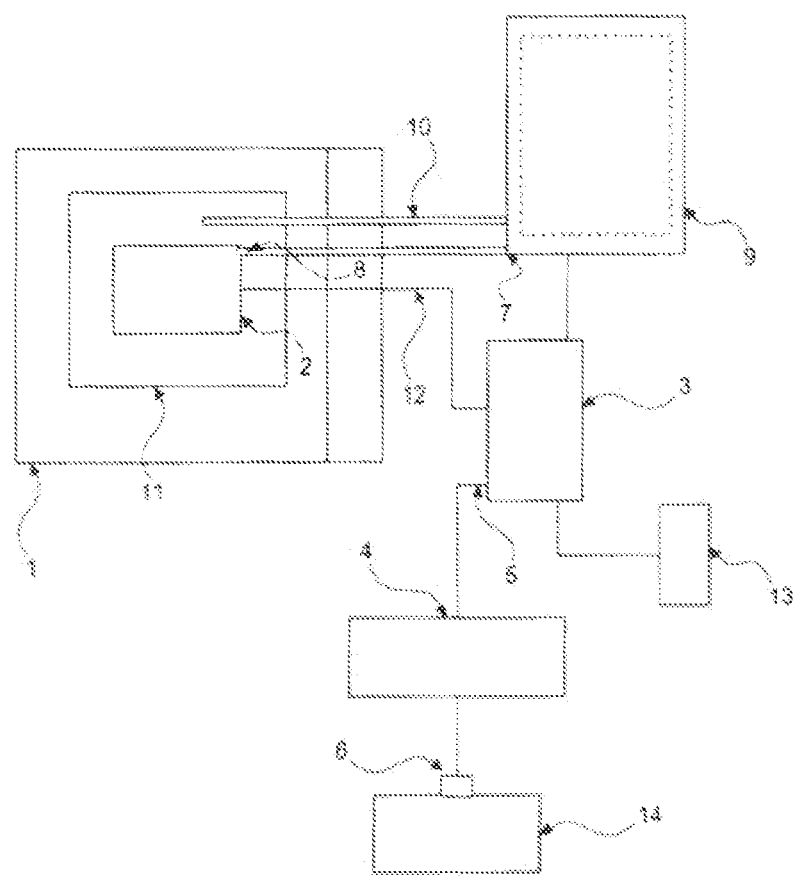

COOLING AND WARMING COVER EMBEDDED WITH TUBING FILLED WITH LIQUID

RELATED APPLICATIONS

The present application claims priority to U.S. Provisional Application No. 62/792,871 filed on Jan. 15, 2019, the contents are which are incorporated herein in their entirety.

BACKGROUND OF THE INVENTION

Cool and Warm cover for human and domestic mammals that provides liquid cooling and/or warming to the body and the temperature of the liquid is controlled by a thermostat. The cover is embedded with tubing which liquid flows throughout emitting cold or warmth to the skin of the wearer. The purpose is to provide a cover that can cool the body from heat and warm the body in cold temperatures covering from the head to toe of the wearer.

Research data shows that from Director of Climate Science at Union of Concerned Scientists stated; As millions of people prepare to face scorching temperatures across the world, scientists are warning, we better brace for more heat moving forward." What that means is that what used to be a rare hot day or high temp record is now the new normal for our summers. The Journal Nature Communications stated that warmer temperatures in the Arctic make severe winters. Study published in Nature Geoscience by a team of researchers-found that unusually cold temperatures in North America and lower precipitation in the south central U.S. all coincided with periods of warmer Artic weather. The extreme cold snaps have gotten more severe in recent years, due to a combination of global warming and a phenomenon you've likely heard of: the polar vortex.

The cover will safely cool and or warm the body from hot and cold temperatures; to help save lives of human and domestic mammals, to provide comfort and relief from babies to adulthood. The benefits of the cover helps prevent sunburns on parts of the body, relieves muscle cramps, hot flashes, prevents hypothermia, prevents hyperthermia, helps circulation, arthritis, relief from hot weather or cold weather, 0 to 3 month old babies (helps maintain safe body temperatures), race car drivers, motorcycle drivers, construction workers, postal carriers, delivery carriers, senior citizens, every day people, comfort at bedtime, comfort to spectators during cold football games and outdoor events. e.g. skiers, runners, walkers, joggers and hunters. The cover helps in power outages in hot or cold weather. Indoors reduces energy costs by regulating the temperatures around the individuals instead of the entire room.

Our covers are interchangeable, electronically operated by battery by USB attachment, solar, and or electrical apparatuses and carried inside auxiliary bag or container that can be attached with a strap to the shoulder, hung across the chest, carried as a backpack, or across the body from all in one. The battery can last up to 10 hours to provide comfort for outdoors activities. The battery can recharge overnight for the next day. You can walk, jog, run, cycle, dance but no contact sports such as football, basketball or soccer.

BRIEF SUMMARY OF THE INVENTION

Accordingly, it is the general purpose of the invention to provide a cooling and or heating system that covers humans and domestic mammals from head to toe. The cover has embedded tubing inside that transmits cool or warm liquid to the cover and recirculates it into a container where the liquid is housed, utilizing a pump for the flow of the liquid. The temperature is controlled by a thermostat that is adjustable in degrees or Celsius by the user and/or operator which is accompanied by an auxiliary bag or container connected for operation of the system. The system that provides the electric current to the pump and the thermostat can be by battery connected to USB connection, solar cells for outdoors and other electrical apparatuses indoors. The user or operator decides what temperature is required and prepares as necessary to cool or warm the liquid with heat packs or cold packs.

BRIEF DESCRIPTION OF THE DRAWINGS

FIG. 1 is a diagrammatic representation of the carrying container/auxiliary bag (1) with an inside view of the container.

(1) carrying bag
(2) pump
(3) thermostat
(4) regulator
(5) wires connecting regulator and thermostat
(6) USB connection
(7) distal end of tubing
(8) valve connection
(9) cover
(10) tubing
(11) container
(12) pump wires
(13) probe
(14) battery

DETAILED DESCRIPTION OF THE OF THE INVENTION

The present invention relates to a cooling and/or warming cover for humans and domestic mammals, which employs a tubing filled with liquid that is cooled or warmed, depending on the application that it is used for. The electronic operation is connected to a pump inside a container, the container is filled with liquid to send it into the tubing which is embedded inside the cover. The pump wire is charged by a battery and/or solar utilizing a USB connection for outdoors activity or electricity indoors. The temperature is controlled by thermostat settings by the user and/or operator. The cool temperature is created by the use of ice packs inside a carrying bag that surrounds the water container inside. The liquid can also have ice cubes placed inside the container that help maintain cool temperatures that transmit to the tubing that flows inside the cover(s) and then recirculates back to the container during operation. This will enable cooling of liquid transferred from the pump, to the tubing inside of the cover to cool from outdoor hot temperatures to provide comfort to the given user. The heating apparatus can use a heating pad charged by battery and/or solar. In addition, but not limited to, the ice packs can be converted to heating packs that surround the outside of the container in the bag. The user can put hot liquid into the container to assist in distributing and recirculating warm liquid from the pump, to the tubing inside the cover and back to the container. This will enable the comfort and warmth outside in a cold environment. The duration of the charge can last up to 10 hours or more on a single battery charge depending on the type of rechargeable battery that is used and its capabilities. Please note that the liquid can be cooled or warmed by numerous ways including but not limited to, cooling and or heating cells, electronic cooling or heating apparatuses, heat can be provided with heat wire modules, and/or peltier with proper voltage attached to container for indoor operations of the cover.

The temperature can be adjusted by the thermostat in degrees and/or Celsius to cool or warm the liquid that is transmitted by the pump and to the tubing during recirculation to the cover and back to the container. The temperature controller thermostat or other measures not limited to, is connected to the auxiliary bag that houses the container with the liquid, with the pump, charger, connectors, tubing outlets and the cooling and heating media mechanisms.

The bag is not limited to design. The bag design can be of user(s) choice. The bag can be carried several ways across the body that is connected to the cover by hand, back pack, shoulders, strap on the body, laid across the body, and in numerous ways to facilitate the utility of the operation in the invention.

The connections of the tubing can be modified to fit any cover of different shapes and sizes, such as not limited to, undergarments, garments in all sizes, bedding, head coverings, head to toe covers to be utilized for humans and domestic mammals with or without multiple attachments. The cooling (cold) systems and warming (heated) systems connected to the cover can be interchangeable to accommodate a variety of covers with numerous fabrics and materials. The covers can be detachable/removed from the container and pump to service other covers such as clothing but not limited to. This invention can be used with the cover and auxiliary bag by walking, running, biking, skiing, car racing, and roller skating, dancing, and other activities. Modifications can be applied for various outdoor and or indoor activities by the manufacturer.

The liquid is put into the container whether it is cold or hot, then the pump is inserted into the liquid. The pump should not be operated without the liquid in the pump because it can burn out the pump operation. The pump has suction cups at the bottom to adhere to the container in order to keep in place during movement of the user. The tubing is connected to the pump, then emerges through the top of the container. The tubing is elongated and attaches to a turn-off valve at the end. The remainder of the elongated tubing should be measured to the appropriate length to provide a format to be embedded into the cover which is diagrammed to be attached to the surface of the cover and then the remaining tubing is placed inside the container top to flow liquid back inside and recirculate the liquid when the pump is turned on. The wires to the pump are taken out through the top of the container. The top of the container is sealed to contain the liquid from coming out of it. The wires from the pump are connected to the thermostat via outside channels, then are connected to a voltage regulator with wires stripped to the outside channels of the thermostat. The other end of the voltage regulator will have a USB connection. The voltage USB connection will be inserted into the battery charger input locator when ready to operate the pump and flow the liquid into the tubing. The user can set the thermostat to the desired temperature. The tubing must be embedded into the cover. A strip of material and or fabric should cover the tubing and secure it in place by sewing, gluing, or attaching via snaps or hook and loop fasteners to the cover. This will provide comfort to the skin and/or fur of the user. The cut-off valve can be placed in several locations on the cover and is not limited to a certain number of units.

In case of a bedding cover that covers the human and/or domestic mammals you can attach a peltier to the container of liquid with various methods and then connect to a voltage regulator with wiring to a toggle switch which contains on, stop, and off functions to control liquid flow and temperature with the wires of the thermostat controller. The auxiliary bag or container houses the container and the electronic components, if preferred, it should have a separate compartment for the battery, an area for the thermostat inside the separate compartment, an outside area for the probe of thermostat to be exposed, and a compartment for phone, wallet and other necessities.

What is claimed is:

1. A portable cooling and warming system comprising:
a fabric cover configured to be placed or worn on a human or a mammal to control temperature, wherein tubing is wound around and embedded into the cover providing pathways for cooled or heated liquid to flow therethrough, wherein the tubing is provided with one or more valves to redirect the flow of the liquid throughout the cover to control a temperature of a portion of the cover for comfort and/or therapeutic purposes, wherein the tubing is attached to the cover by a strip of fabric that is secured to an interior of the cover and is configured to be a protective layer between the tubing and a body of a wearer;
a sealable container that is configured to recirculate the liquid from the container, through container tubing and to the tubing of the cover, wherein the container houses a pump, wherein the pump has a bottom with suction cups, wherein the suction cups attach to the container to hold the pump in place during use, wherein the container tubing is connected to the pump within the container and extends through a top opening of the container, the container tubing emerges from the top opening and releasably attaches to the tubing of the cover;
a thermostat is connected to the pump with wires that extend from the pump through the top of the container and to outside channels of the thermostat, wherein the thermostat is programmable and configured to adjust a temperature of the liquid transmitted by the pump to the container tubing and to the tubing of the cover; and
a carrying bag having an attached carrying strap that is configured to be carried by the wearer, wherein the carrying bag comprises a first compartment which houses the container, a second separate compartment which houses the battery and the thermostat, and a third separate compartment configured to house personal necessities, wherein the carrying bag has an opening in the second compartment through which a probe of the thermostat extends to be positioned on an outside of the carrying bag.

* * * * *